United States Patent [19]

Bhise et al.

[11] Patent Number: 4,508,927

[45] Date of Patent: Apr. 2, 1985

[54] PREPARATION OF GLYCOLS FROM ETHYLENE OXIDE

[75] Inventors: Vijay S. Bhise, Bloomfield, N.J.; Harold Gilman, Millwood, N.Y.

[73] Assignee: The Halcon SD Group, Inc., New York, N.Y.

[21] Appl. No.: 519,653

[22] Filed: Aug. 2, 1983

[51] Int. Cl.$^3$ .................. C07C 29/00; C07C 31/20
[52] U.S. Cl. .................. 568/858; 549/450; 549/538
[58] Field of Search .................. 568/858

[56] References Cited

U.S. PATENT DOCUMENTS

| | | | |
|---|---|---|---|
| 3,214,892 | 11/1965 | Holbrook et al. | |
| 3,629,343 | 12/1971 | Zaharovich et al. | 568/867 |
| 3,964,980 | 6/1976 | Ozero | 568/867 |
| 4,117,250 | 9/1978 | Foster et al. | 568/858 |
| 4,160,116 | 7/1979 | Mieno et al. | 568/867 |
| 4,221,727 | 9/1980 | Tsang et al. | |
| 4,233,221 | 11/1980 | Raines et al. | |
| 4,237,324 | 12/1980 | Raines et al. | 568/858 |
| 4,314,945 | 2/1982 | McMullen et al. | 568/858 |
| 4,400,559 | 8/1983 | Bhise | 568/858 |

FOREIGN PATENT DOCUMENTS 2107712 10/1982 United Kingdom .

*Primary Examiner*—J. E. Evans
*Attorney, Agent, or Firm*—Riggs T. Stewart; William C. Long; Harold N. Wells

[57] ABSTRACT

A process for preparation of glycols in which the vapor remaining after the partial condensation of a conventional ethylene oxide stripper overhead vapor stream is contacted with an aqueous solution of ethylene carbonate to recover ethylene oxide. No water need be removed from the enriched ethylene carbonate stream. Carbon dioxide is added and ethylene carbonate is formed by reaction at about 50° to 200° C. and 5 to 150 kg/cm$^2$ gauge in the presence of a suitable catalyst, preferably about 0.5–20 wt % of an organic phosphonium halide. After stripping off unreacted components, the ethylene carbonate is hydrolyzed to glycols in the presence of the same carbonation catalyst and at temperatures in the range of about 100° to 200° C. and pressures of about 5 to 150 kg/cm$^2$ gauge. Optionally, ethylene oxide and ethylene carbonate may be co-produced.

8 Claims, 2 Drawing Figures

PREPARATION OF GLYCOLS FROM ETHYLENE OXIDE

PRIOR ART

This invention relates generally to the preparation of glycols from ethylene oxide. Traditionally, this has been done by hydration of ethylene oxide with water. A large excess of water is used in order to minimize the amounts of higher glycols which would otherwise form. However, the removal of excess water penalizes the process. Thus, in recent years the preparation of glycols from ethylene oxide by other routes has been the subject of many patents. Many of these involve the presence of carbon dioxide, which has the effect of reducing the formation of higher glycols and, consequently, permitting the use of smaller amounts of water, approaching the theoretical 1:1 ratio. It has been postulated by some that ethylene carbonate is formed as an intermediate compound in such a one-step process, though it is not usually reported as present in the glycol product, nor would it be desired. Other processes react ethylene oxide with carbon dioxide to form ethylene carbonate, and then in a separate step, the ethylene oxide is hydrolyzed to form ethylene glycols. An example of the one-step process is U.S. Pat. No. 4,160,116 assigned to Showa Denka, while a two-step process is shown in Union Carbide's U.S. Pat. No. 4,117,250 and U.S. Pat. No. 4,314,945. It is of interest to note the opinion of the patentees in U.S. Pat. No. 4,117,250 that if the two-step process is carried with water in the first step (as disclosed in U.S. Pat. No. 3,629,343) ethylene carbonate is not actually produced in the first step, but that the ethylene glycol is derived from hydrolysis of ethylene oxide.

Ethylene carbonate preparation has been the subject of a number of patents. It has solvent properties and is potentially a convenient means of transporting ethylene oxide. Patents which are directed to preparation of ethylene carbonate are discussed in pending applications having Ser. Nos. 326,447, 441,191, and 388,395, which show preparation of ethylene carbonate in the presence of water.

In U.S. Pat. No. 3,214,892, Holbrook shows that ethylene carbonate is useful for absorbing carbon dioxide from gases. In a more recent patent, U.S. Pat. No. 4,221,727, Tsang, et al., show that ethylene carbonate may be used to absorb ethylene oxide from the effluent of the reactor in which the ethylene oxide has been produced. Thereafter, ethylene oxide is stripped from the ethylene carbonate with an inert gas, such as carbon dioxide or nitrogen and the ethylene carbonate stream returned to scrub additional ethylene oxide. The overhead from the ethylene oxide stripper is shown in the companion of the Tsang patent (U.S. Pat. No. 4,233,221 to Raines, et al.) to be useful feed for the preparation of ethylene carbonate. They teach that it is sufficient to merely compress the stripper overhead gas and then cool it in order to remove the water which is present before forming ethylene carbonate. Tsang, et al., cite a number of advantages for the use of ethylene carbonate as an absorbing media. First, it has a greater ability to absorb both ethylene oxide and carbon dioxide than does water, which is conveniently used. It also is capable of picking up more carbon dioxide as Holbrook taught. In addition, ethylene carbonate has a lower specific heat than water, and thus the heat load on the stripping column is said to be reduced. It is also stated that ethylene is not absorbed to any great extent by ethylene carbonate.

After careful study of the process proposed by Tsang, et al., we have concluded that it suffers from serious deficiencies and consideration of these problems led to the discovery of our invention to be described later. With the use of a scrubbing medium, other than water the ethylene oxide catalyst may be contaminated by the scrubbing medium. Consequently, adoption of the proposed process of Tsang, et al., should be cautiously approached. It also appears that, contrary to the patentees statement, ethylene solubility in ethylene carbonate is not insignificant, and the loss of ethylene would be substantial. It should be understood that in a typical ethylene oxide process, only a relatively small amount of ethylene is reacted in each pass. Consequently, the recycle gases contain large quantities of ethylene. If absorbed in the ethylene carbonate and carried into the stripper, the ethylene would be found in the ethylene oxide produced and require additional separation facilities in order to avoid losing it.

A particularly serious difficulty with the Tsang process is disposing of the by-product water absorbed by the solution. For each mol of ethylene oxide produced, approximately 0.5 to 1 mol of water would also be formed, depending upon the selectivity of the reaction. This water must be removed. In the Tsang patent, Table 2 indicates that the absorbate contains roughly equivalent portions of ethylene oxide and water and a significant quantity of ethylene oxide remains after stripping. Although stripping conditions can be adjusted to reduce ethylene oxide in the circulating absorbent, a purge of the by-product water cannot be made from the recirculating lean absorbent without losing ethylene carbonate. Substantial amounts of ethylene oxide and ethylene carbonate present would have to be recovered, complicating the process. However, if not purged, the water which is picked up in the absorber would be rejected overhead in the stripper. Thus, this will be approximately 0.5 to 1 mols of water for each mol of ethylene oxide. The water level in the ethylene carbonate absorbent would continually increase as it circulates between the absorber and the stripper until the amount of water produced by the reaction is rejected overhead by the stripper. Furthermore, if the water is rejected overhead in the stripper, and the gas is condensed and cooled the water condensed out would contain substantial amounts of ethylene oxide. If the condensed water is purged intolerable losses of ethylene oxide would result, again requiring additional recovery facilities. In fact, it appears that in order to purge by-product water, it would be necessary to recover some ethylene oxide.

In a recent published British patent application, G.B. 2,107,712A, the use of an intermediate absorbent is abandoned and the ethylene oxide reactor effluent is sent to a reactor where ethylene carbonate is formed so that ethylene oxide is not recovered as such. Unreacted gases are recycled to the ethylene oxide reactor, which may contaminate the catalyst. Other disadvantages of this scheme appear to be the corrosion resulting from the use of sodium iodide as a catalyst. In addition, since oxygen is present, it is likely that the iodide will be oxidized to iodine.

As will be seen, our invention avoids these difficulties and provides a stream which is suitable for formation of ethylene carbonate and then hydrolysis of the ethylene carbonate to glycols in a separate step. Our process employs the absorption-stripping system shown by Ozero in U.S. Pat. No. 3,964,980, which permits purging water produced in the ethylene oxide reaction from the recirculating aqueous absorbent stream. At the same time, the amount of water in the overhead vapor from the stripper is suitable for feed to an ethylene glycol process according to our invention. The composition of this gas (line 63 in Ozero's FIG. 2), is shown to be highly concentrated in ethylene oxide and provides an ideal feedstream for our process.

SUMMARY OF THE INVENTION

Glycols are prepared from ethylene oxide via an ethylene carbonate intermediate. The effluent of a reaction where ethylene has been combined with molecular oxygen over a supported silver catalyst to form ethylene oxide is scrubbed with an aqueous stream. The absorbed ethylene oxide is stripped from the enriched aqueous solution in the conventional manner. The vapor produced is partially condensed to remove the bulk of the water as liquid, which is returned to the stripping column as reflux or withdrawn in part for recovery of the ethylene oxide content. The remaining vapor, which should comprise about 50 to 95 mol % ethylene oxide and 5 to 50 mol % water (as determined by the condenser temperature) is absorbed in a recirculating aqueous stream containing ethylene carbonate, ethylene glycol and catalyst. Since the proportions of the enriched absorbant stream are suitable, it is necessary only to add carbon dioxide and react the mixture in the presence of a suitable catalyst, preferably an organic phosphonium halide, to produce ethylene carbonate from the absorbed ethylene oxide. The reaction takes place at temperatures in the range of about 50° to 200° C. and at pressures in the range of about 5 to 150 kg/cm$^2$ gauge, preferably 5-75 kg/cm$^2$ gauge and with a catalyst concentration of about 0.5-20 wt %, preferably 1-5 wt %. After forming ethylene carbonate, unreacted components are stripped off, about 1 to 5 mols of water is added for each mol of ethylene carbonate, and glycols are formed by hydrolysis of the ethylene carbonate at temperatures in the range of about 100° to 200° C. and pressures in the range of about 5 to 150 kg/cm$^2$ gauge, preferably 5-15 kg/cm$^2$ in the presence of the same catalyst. The glycols formed are recovered by conventional distillation and the catalyst is recirculated to the carbonation reaction. As desired ethylene oxide and/or ethylene carbonate may be co-produced.

The process of our invention obtains significant advantages over processes of the prior art, which propose scrubbing the effluent of the ethylene oxide reactor with ethylene carbonate. The ratio of ethylene oxide to water in the ethylene oxide stripper overhead vapor can be adjusted to make it possible to simplify the processing to glycols and to avoid difficulties associated with prior art processes.

DESCRIPTION OF THE INVENTION

Figure 1:
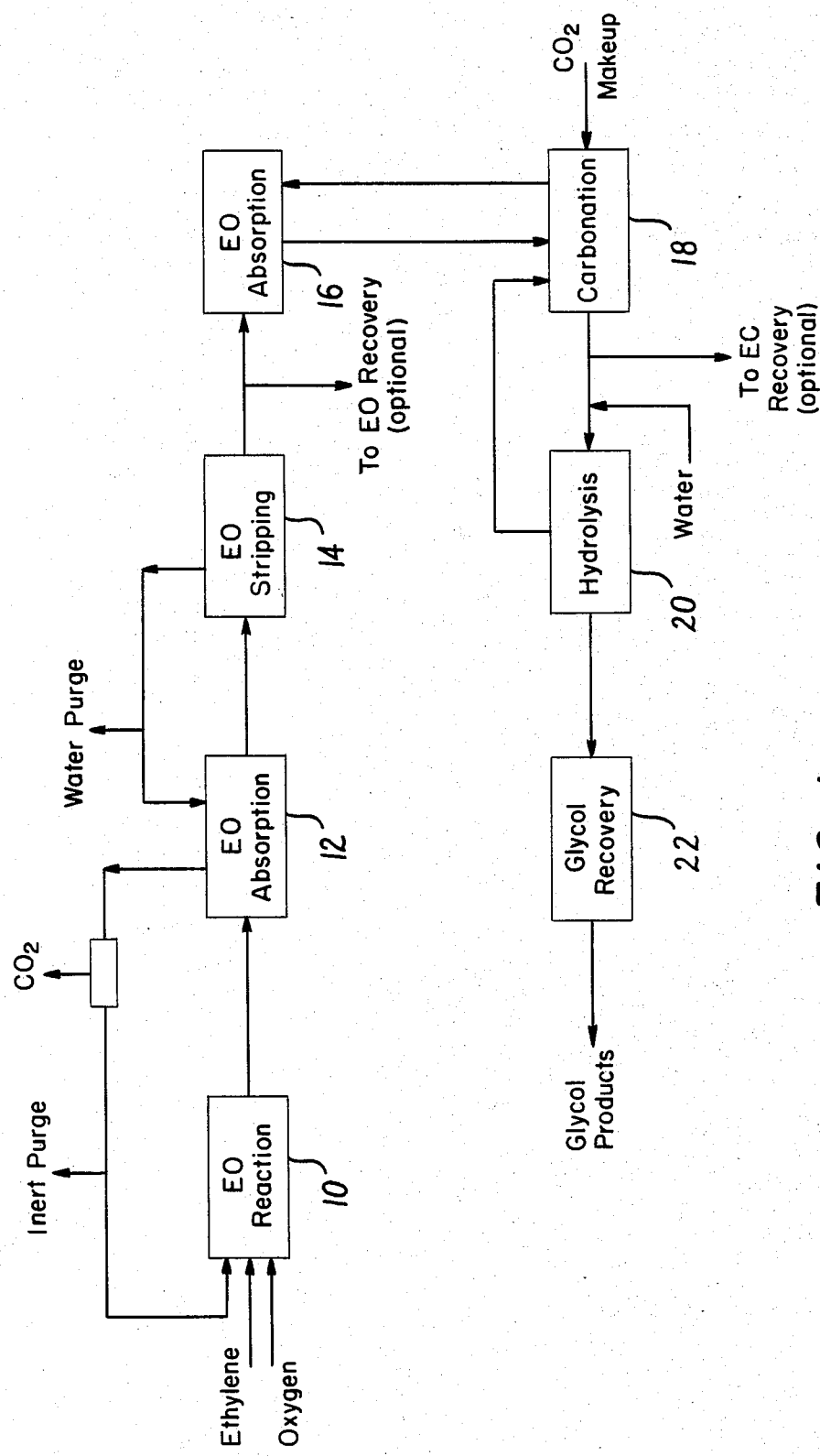
FIG. 1 is a block diagram showing the process of the invention.

The process of the invention is schematically described in the block diagram shown in FIG. 1. In this process, facilities are shown for ethylene carbonate recovery, which is an optional addition to the principal process for preparation of glycols. Ethylene and a source of oxygen enter an ethylene oxide reactor 10 where they are reacted to form ethylene oxide over a supported silver catalyst. Conditions are typical of the art, namely, about 200°-400° C. and 10-40 kg/cm$^2$ gauge. About 1-20% of the ethylene passed is converted into ethylene oxide with the remainder being recovered and recycled to the reactor. Concentration of ethylene in the reactor feed is approximately 5-20% and oxygen 5-15%, the remainder being various inert gases the composition of which depends particularly upon the source of oxygen used in the particular reaction system. Leaving the reactor the gases contain only about 0.5-5% ethylene oxide, which is absorbed (12) by a recirculating aqueous solution in a conventional absorber tower. Non-absorbed gases are recirculated to the reactor after removal of carbon dioxide and any purge of other inert gases as necessary. The enriched absorbent is passed to the stripper (14) where at higher temperatures and lower pressures ethylene oxide is released. In the process of the invention this ethylene oxide is processed into ethylene glycols via ethylene carbonate. The stripped aqueous solution is recirculated to the ethylene oxide absorber. Water produced in the reaction as a by-product is purged from this recirculating stream. Although not specifically shown here, the overhead vapor from the stripper is partially condensed and the liquid portion is returned as reflux to the stripper. Alternatively, a portion of the liquid may be fed to facilities for ethylene oxide recovery and purification. The vapor which is separated after partial condensation contains ethylene oxide and water which are further processed according to the invention. These gases are then absorbed (16) by a recirculating aqueous stream containing ethylene carbonate, ethylene glycol, and catalyst in a conventional vapor-liquid contacting tower and then passed directly to a carbonation reactor (18) where, in the presence of a suitable catalyst, preferably an organic phosphonium halide, ethylene oxide is converted to ethylene carbonate. Carbon dioxide needed for the reaction may be derived from various sources. Where the ethylene carbonate is used to produce ethylene glycols, the carbon dioxide split off during hydrolysis may be recycled to the carbonation reactor from the hydrolysis reactor (20) as shown. The net product of the carbonation reactor (18) is passed to the hydrolysis reactor (20) and water added. The same catalyst used for the carbonation reaction is used for the hydrolysis, which simplifies the process and is an advantage over the prior art which employs two catalysts. If ethylene carbonate is a desired product, it may be recovered by distillation from stream (19) which would otherwise be passed to hydrolysis. After hydrolysis, the glycols are sent to a recovery section (22) where by distillation, glycols are separated and purified.

A particularly important aspect of the invention is the discovery that by properly selecting a feedstream for ethylene carbonate and/or glycols production, it is possible to operate an ethylene oxide plant in the conventional manner without introducing additional recovery steps or risking contamination, which is inherent to processes such as those previously discussed where the ethylene oxide reactor effluent is either scrubbed by ethylene carbonate directly or passed into a carbonation reactor.

Figure 2:
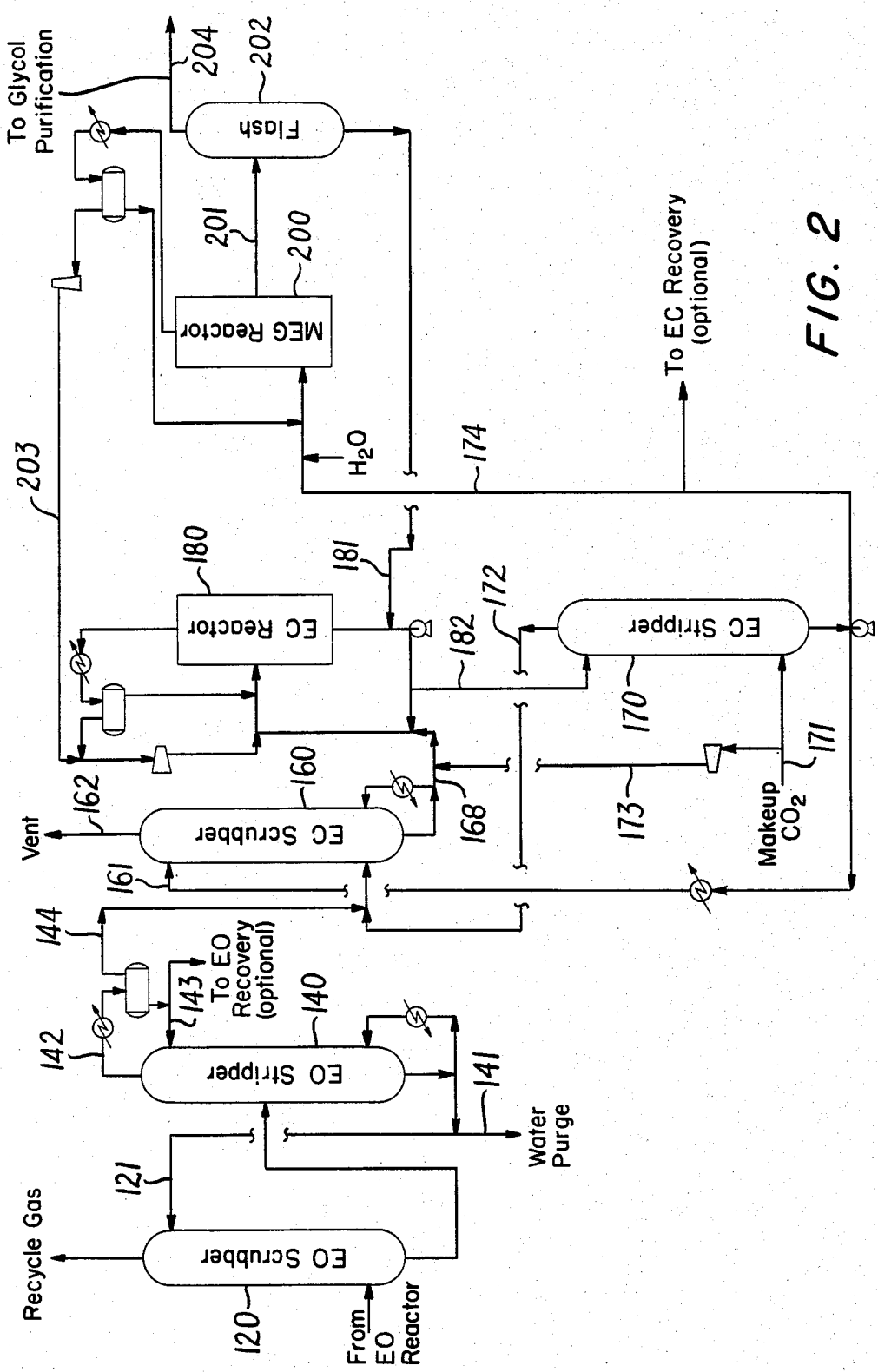
FIG. 2 is a flowsheet showing an embodiment of the invention.

Details of a process scheme according to the invention and consistent with the block diagram of FIG. 1 is shown as FIG. 2. Effluent from the ethylene oxide reactor is scrubbed in tower (120) by a recirculating aqueous stream (121) and is stripped in tower (140) according to the conventional process as described in the Ozero patent previously mentioned. It will be seen that water may be purged (141) from the recirculating aqueous stream (121) after the ethylene oxide has been stripped out. Partial condensation of the overhead (142) from the ethylene oxide stripper (140) removes a significant amount of water by condensation which is returned to the stripper (140) via line (143) and eventually is removed by the purge (141). Alternatively, if desired, some or all of the liquid stream may be diverted to ethylene oxide recovery facilities. The quantity of water which passes with the ethylene oxide vapor (144) from the separator is in proportions which are highly suitable for the carbonation and hydrolysis reactions to come. By adjusting the condenser temperature, vapor stream (144) comprises about 50 to 95 mol % ethylene oxide and 5 to 50 mol % water as the stream enters an ethylene carbonate scrubber (160), which may be a conventional vapor-liquid contacting tower, where it passes countercurrently to an aqueous stream (161) containing ethylene carbonate, ethylene glycol and catalyst from the ethylene carbonate stripper (170) in order to absorb the ethylene oxide. Waste gases are vented (162) from the top of the scrubber (160) and may be recovered as desired. Operating conditions in the scrubber 160 are about 35°–45° C. at the top and about 45°–75° C. at the bottom with the average pressure being about 1–2 kg/cm$^2$ gauge. When operated adiabatically, the temperature will be higher at the bottom than the top, but alternatively cooling may be provided to control the tower bottom temperature. The liquid stream containing ethylene oxide is then passed to the ethylene carbonate reactor 180 where at a temperature of about 50°–200° C. and pressure of about 5–75 kg/cm$^2$ the ethylene oxide is reacted with carbon dioxide to form the carbonate in the presence of a suitable catalyst. Since water is present a small amount of ethylene glycol is also formed. Although other catalysts may be used, such as known to the art including organic ammonium halides, inorganic halides, and the like, preferably an organic phosphonium halide is employed since such compounds have particular benefits when the reaction is carried out in the presence of water. The amount of catalyst may be about 0.5 to 20 wt percent, preferably 1–5 wt percent. The catalyst enters the ethylene carbonate reactor (180) as part of stream (181) which is recovered during the purification of ethylene carbonate. Carbon dioxide comes in large part from the hydrolysis reactor (200) where the ethylene carbonate reacts with water to form ethylene glycol. The net product of the glycol reactor (201) is then flashed (202) to separate the bulk of the carbon dioxide which is then compressed and recirculated via stream (203) as shown. Any makeup carbon dioxide (171) needed is supplied from a source outside the process of the invention and enters the bottom of the ethylene carbonate stripper (170) and is recirculated to the ethylene carbonate scrubber (160) via line (172) or it is compressed and fed to the ethylene carbonate reactor (180) via stream (173). As shown, low boiling compounds are cooled and returned to the reactor (180), but alternatively some could be vented to the scrubber (160).

Ethylene carbonate formed in reactor (180) is recovered by passing the product stream (182) to the carbonate stripper (170) as shown. Any gas present is returned to the ethylene carbonate scrubber (160). If it is desired to produce ethylene carbonate it may be recovered by distillation (not shown).

All or a portion of the net ethylene carbonate produced in reactor (180) passes to the hydrolysis reactor (200) via stream (174). Hydrolysis is carried out at a temperature of about 100°–200° C. and 5–75 kg/cm$^2$ gauge in the presence of the same catalyst which has been used for formation of ethylene carbonate. About 1 to 5 mols of water per mol of ethylene carbonate will be used. The ethylene glycols are separated by a flash (202) which removes the heavy materials and catalyst for recycle via stream (181). The product glycols are sent via stream (204) to conventional distillation facilities (not shown), which separate monoethylene glycol from higher glycols and purifies those products. The following example provides a specific instance of the process of the invention according to FIG. 2, but without recovery of ethylene carbonate as such.

EXAMPLE

One thousand mols/hr of a vapor stream (144) from the ethylene oxide stripper (140), containing 77.8% ethylene oxide, 13.7% water, and 5.7% carbon dioxide, the remainder being inerts and minor by-products is combined with 800 mols/hr of a stream (172) from the ethylene carbonate stripper (170), which contains 15% ethylene oxide, 58% carbon dioxide, and 27% water. The combined vapor stream is scrubbed with 9660 mols/hr of a recirculating aqueous stream (161) containing 9.5% water, 80.3% ethylene carbonate, 9.2% monoethylene glycol, and 1.0% heavier glycols and catalyst. The vapor (162) removed from the top of the scrubbing column (160) contains 510 mol/hr carbon dioxide and the inerts from stream (144). The tower (160) operates at about 1.2 kg/cm$^2$ gauge. The liquid leaving the bottom of the tower is controlled at about 48° C. A stream (168) is passed to the ethylene carbonate reactor (180) totalling 10,924 mol/hr and containing 8.2% ethylene oxide, 11.6% water, 71.0% ethylene carbonate, 8.1% monoethylene glycol, and the remainder being heavier glycols and catalyst. In reactor (180), at 35 kg/cm$^2$ gauge and 170° C., the fresh ethylene oxide is reacted with 726.5 mol/hr of carbon dioxide using 0.8% methyl triphenyl phosphonium iodide cataxyt. About 52 mol/hr of ethylene glycol is also formed. A net product stream (182) is withdrawn and passed to the ethylene carbonate stripper (170), where at about 1.5 kg/cm$^2$ gauge and 165°–170° C. the ethylene carbonate is stripped by 450 mol/hr of carbon dioxide (171). Stripped liquid is recycled to the ethylene carbonate scrubber (160), except for the net product, 904 mol/hr, which is sent to the hydrolysis reactor (200), where at 10 kg/cm$^2$ gauge and 180° C., the ethylene carbonate is hydrolyzed to ethylene glycols with 1453 mol/hr of water. Carbon dioxide liberated is disengaged and cooled to condense vaporized water and ethylene glycol which are recycled to the hydrolysis reactor, while the carbon dioxide is recycled to the carbonation reactor via stream (203). The net liquid product of the reactor, 1313 mol/hr, contains 38.6% water, 60.0% monoethylene glycol, 1.5% heavier glycols and catalyst. It is flashed in vessel (202), with the overhead vapor, 1273 mol/hr, containing all of the water and the net production of the monoethylene glycol and the higher glycols being sent to purification facilities (not shown), while the heavier glycols and catalyst are recycled to the ethylene carbonate reactor (180).

We claim:

1. A process for preparing ethylene glycols comprising:

(a) reacting ethylene with molecular oxygen in the vapor phase over a supported silver catalyst to produce an effluent comprising ethylene oxide, unreacted ethylene, carbon oxides and water;

(b) scrubbing said effluent of (a) with a recirculating aqueous stream to absorb the ethylene oxide formed in said reaction of (a) to produce an enriched aqueous stream;

(c) stripping at a lower pressure than the scrubbing of (b) in a first vapor-liquid contacting column the enriched aqueous stream of (b) to remove the absorbed ethylene oxide therefrom in a vapor stream, and returning the stripped aqueous stream to step (b);

(d) partially condensing the ethylene oxide-containing vapor stream of (c) to remove the bulk of the water therefrom, separating water-containing liquid condensed therefrom, and returning said liquid as reflux to said first column;

(e) scrubbing the ethylene oxide-containing vapor after separating said condensed water in a second vapor-liquid contacting column with an aqueous solution comprising ethylene carbonate, ethylene glycol, and carbonation catalyst to absorb substantially all of the ethylene oxide and water content of said vapor to form an enriched ethylene carbonate solution;

(f) adding carbon dioxide to said enriched solution of (e) and thereafter reacting ethylene oxide and carbon dioxide contained in said solution in the presence of an effective amount of a carbonation catalyst to form ethylene carbonate;

(g) stripping the reacted solution of (f) to remove unreacted ethylene oxide and carbon dioxide therefrom, dividing the stripped solution in at least two portions, and recirculating the first portion as scrubbing solution to step (e);

(h) adding water to the second portion of the stripped solution of (g) and reacting ethylene carbonate with water in the presence of said carbonation catalyst to form ethylene glycols; and (i) separating the ethylene glycols formed in (h) and returning said carbonation catalyst to step (f).

2. The process of claim 1 wherein the ethylene oxide-containing vapor of (e) contains 50 to 95 mol % ethylene oxide and 5 to 50 mol % water vapor.

3. The process of claim 1 wherein said catalyst of (f) is 0.5 to 20 weight percent of an organic phosphonium halide.

4. The process of claim 1 wherein the water added in (h) is 1 to 5 mols for each mol of ethylene carbonate.

5. The process of claim 1 wherein said ethylene carbonate formation of (f) is carried out at a temperature in the range of about 50° to 200° C. and at pressures in the range of about 5 to 75 kg/cm$^2$ gauge.

6. The process of claim 1 wherein said ethylene glycol formation of (h) is carried out at a temperature in the range of about 100° to 200° C. and at pressure in the range of about 5 to 75 kg/cm$^2$ gauge.

7. The process of claim 1 wherein ethylene oxide is recovered from a portion of the condensed liquid of (d).

8. The process of claim 1 wherein ethylene carbonate is recovered from a portion of the stripped solution of (g).

* * * * *